(12) United States Patent
Gauer et al.

(10) Patent No.: US 9,023,658 B2
(45) Date of Patent: May 5, 2015

(54) ACOUSTIC CONCENTRATION METHOD AND DEVICE AND A REACTION METHOD

(75) Inventors: Christoph Gauer, Munich (DE); Wolfgang Mann, Neudrossenfeld (DE)

(73) Assignee: Beckman Coulter, Inc, Brea, CA (US)

( * ) Notice: Subject to any disclaimer, the term of this patent is extended or adjusted under 35 U.S.C. 154(b) by 1428 days.

(21) Appl. No.: 12/083,792

(22) PCT Filed: Sep. 27, 2006

(86) PCT No.: PCT/EP2006/009392
§ 371 (c)(1),
(2), (4) Date: Apr. 22, 2009

(87) PCT Pub. No.: WO2007/045336
PCT Pub. Date: Apr. 26, 2007

(65) Prior Publication Data
US 2009/0227042 A1  Sep. 10, 2009

(30) Foreign Application Priority Data
Oct. 19, 2005  (DE) .......... 10 2005 050 167

(51) Int. Cl.
G01N 33/566 (2006.01)
G01N 1/40 (2006.01)
G01N 35/00 (2006.01)

(52) U.S. Cl.
CPC .......... *G01N 1/40* (2013.01); *G01N 2001/4094* (2013.01); *G01N 2035/00554* (2013.01)

(58) Field of Classification Search
None
See application file for complete search history.

(56) References Cited

U.S. PATENT DOCUMENTS

| | | | |
|---|---|---|---|
| 4,055,491 A | 10/1977 | Porath-Furedi | |
| 4,307,070 A * | 12/1981 | Oberhardt et al. | 436/500 |
| 4,370,030 A * | 1/1983 | Sprague | 359/311 |
| 4,521,521 A * | 6/1985 | Abbott et al. | 436/517 |
| 4,877,516 A | 10/1989 | Schram | |
| 4,960,715 A | 10/1990 | Hadfield et al. | |
| 5,147,562 A * | 9/1992 | Heyman | 210/748.02 |
| 5,225,089 A * | 7/1993 | Benes et al. | 210/748.05 |
| 5,313,202 A * | 5/1994 | Hansman et al. | 340/962 |
| 5,375,653 A * | 12/1994 | Borlinghaus et al. | 165/109.1 |
| 6,048,699 A | 4/2000 | Foley et al. | |
| 6,216,538 B1 * | 4/2001 | Yasuda et al. | 73/570.5 |
| 6,221,258 B1 | 4/2001 | Feke et al. | |
| 6,275,603 B1 * | 8/2001 | Cronshaw et al. | 382/142 |
| 6,332,541 B1 | 12/2001 | Coakley et al. | |
| 6,887,384 B1 | 5/2005 | Frechet et al. | |
| 7,459,304 B2 * | 12/2008 | Gauer | 435/287.2 |
| 7,527,740 B2 * | 5/2009 | Effenhauser et al. | 210/806 |
| 2001/0019702 A1 * | 9/2001 | Watari et al. | 422/67 |
| 2002/0083771 A1 * | 7/2002 | Khuri-Yakub et al. | 73/589 |

(Continued)

FOREIGN PATENT DOCUMENTS

DE  195 41 417   5/1997
DE  101 17 771   10/2002

(Continued)

*Primary Examiner* — Bao-Thuy L. Nguyen
*Assistant Examiner* — Richard Moerschell
(74) *Attorney, Agent, or Firm* — Kilpatrick Townsend & Stockton LLP

(57) ABSTRACT

A method for concentrating materials in a liquid involves pouring the liquid into a material-containing receptacle and irradiating the liquid by acoustic waves so that a stationary flow pattern with different flow rate areas is formed in the receptacle. A concentration device and reaction method using such concentration are also provided.

15 Claims, 1 Drawing Sheet

(56) References Cited

U.S. PATENT DOCUMENTS

| | | | |
|---|---|---|---|
| 2002/0162393 A1* | 11/2002 | Kaduchak et al. | 73/570.5 |
| 2003/0170664 A1* | 9/2003 | Mori et al. | 435/6 |
| 2004/0042915 A1* | 3/2004 | Rife et al. | 417/321 |
| 2004/0147043 A1 | 7/2004 | Boer et al. | |
| 2004/0219056 A1* | 11/2004 | Tribelsky et al. | 422/22 |
| 2005/0037507 A1* | 2/2005 | Gauer | 436/163 |
| 2006/0005956 A1* | 1/2006 | Kester | 165/151 |
| 2006/0037915 A1* | 2/2006 | Strand et al. | 210/748 |
| 2006/0257287 A1* | 11/2006 | Call et al. | 422/83 |
| 2008/0225634 A1* | 9/2008 | Murakami | 366/114 |

FOREIGN PATENT DOCUMENTS

| | | | | |
|---|---|---|---|---|
| EP | 0773055 | | 5/1997 | |
| EP | 773055 A2 * | | 5/1997 | B01D 43/00 |
| GB | 2308 182 | | 6/1997 | |
| WO | 93/16814 | | 9/1993 | |
| WO | 98/17373 | | 4/1998 | |
| WO | WO 2005/072854 | * | 2/2005 | G01N 1/28 |
| WO | 2005/072854 | | 8/2005 | |
| WO | WO 2005/072854 | * | 8/2005 | G01N 1/28 |
| WO | 2005/124300 | | 12/2005 | |

* cited by examiner

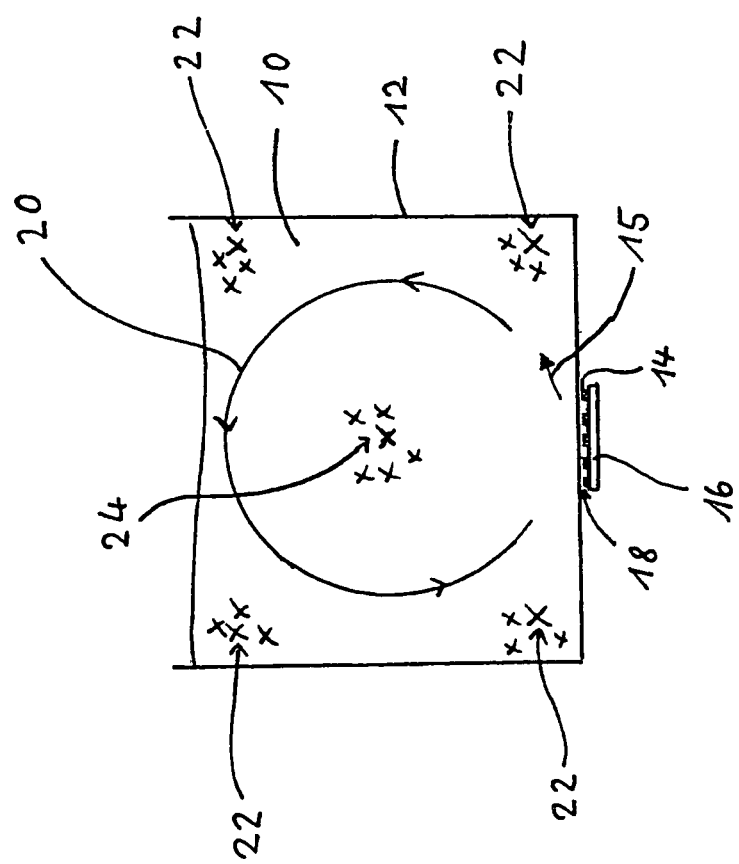

ACOUSTIC CONCENTRATION METHOD AND DEVICE AND A REACTION METHOD

BACKGROUND OF THE INVENTION

The invention relates to a concentration method for the concentration of material in a liquid, to a concentration device for the carrying out of the method and to a reaction method using the concentration method.

Especially in biological research or diagnostics, the problem frequently arises of having material particles, in particular cells or co-called beads, react with one another or with biological macromolecules such as nucleic acids, proteins, antigens, antibodies, etc. Beads designate microspheres of a diameter of some 100 nm up to some μm onto which a reaction starting material is coated. An example for these are latex agglutination assays such as are described in U.S. Pat. No. 4,960,715. There, latex spheres are used as beads having a diameter of some 100 nm up to some μm and are coated either with antigens or antibodies. Either antibodies or antigens are then accordingly detected in the liquid sample which react with the molecules on the beads and which can link the beads to one another. This so-called agglutination or aggregation can be evaluated optically and serves for the detection of the presence of the antibodies or antigens in the sample. In the present text, the term "reaction" should, where applicable, also include the linking process between the beads.

The material particles in the liquid which should react with one another come together based on diffusion. This process can be reinforced by active mixing or agitating.

It would be desirable for the individual material particles to be brought close to one another in the solution to increase the reaction probability. This can e.g. be achieved by a sufficiently high concentration of particles in the solution. Frequently, however, sufficient material is not available to achieve a desirably high concentration. This problem is in particular also encountered when cell-cell interacts in a solution, the reaction of cells with coated beads or of differently coated beads with one another should be examined.

It is also desirable in some applications to achieve a concentration of material particles in a solution independently of a reaction in which the reaction starting materials should be brought close to one another.

A known method for concentration is the use of filters, membranes or other porous media such as is described in U.S. Pat. No. 6,887,384. However, with a filter, non-specific reactions with the filter wall can occur and as a rule transmission measurements at the concentrated medium are impossible.

Another possibility for concentration is centrifugation such as used in the enrichment of uranium. For this purpose, a reaction vessel must be introduced into a centrifuge and be removed from it again after the centrifugation to be able to carry out a measurement so that the method is complex and/or expensive.

SUMMARY OF THE INVENTION

It is the object of the present invention to provide a method for the concentration of material in a liquid which can be carried out simply and cost-effectively and which, optionally, also allows measurements directly in the concentration vessel.

This object is satisfied by a concentration method for the concentration of material in a liquid having the features herein. A reaction method for the reaction of at least two reaction starting materials in a liquid uses this concentration method in accordance with the invention. Additionally, a concentration device for carrying out of the method is the subject of the invention. Preferred embodiments are also disclosed herein.

In the concentration method in accordance with the invention, a liquid is introduced with material located therein into a vessel and acoustic waves are radiated into the liquid such that a stationary flow pattern with regions of different flow speed arise in the vessel. Material particles, e.g. cells or beads, collect and concentrate in regions of the liquid in which the flow speed is minimal, in particular where it is equal to zero. In this manner, particles can be brought into direct proximity with one another, which results in a concentration with increased local concentration in these regions. Unlike when acoustic waves are used for the homogenization, for the agitating or for the mixing of liquid in which a non-stationary flow pattern is desired and is e.g. generated by varying the amplitude and/or the frequency of the waves radiated in, the concentration method in accordance with the invention is based on the use of a stationary flow pattern which can e.g. be achieved in that the amplitude and/or frequency of the acoustic waves radiated is/are kept constant.

The material to be concentrated in the liquid comprises e.g. cells, coated beads, particles or other reaction starting materials.

This already results in a collection of the material in these regions when regions are generated in the vessel by the stationary flow pattern in which the flow speed is lower than in the surroundings. It is particularly advantageous when regions are produced with a flow sped close to zero, preferably equal to zero.

The radiation location and the radiation direction of the acoustic waves are dependent on the vessel shape used and can e.g. be optimized experimentally. As a rule, it is sufficient for acoustic waves to be coupled in at one point of the vessel and in one direction. However, applications are also possible in which acoustic waves are radiated into the liquid at different points and/or in different directions to generate a concentration in specific desired regions of the vessel.

Acoustic waves can e.g. be generated with the help of a piezoelectric volume oscillator which is located at the vessel wall or is integrated in the vessel wall. The use of at least one interdigital transducer such as is known from radio frequency filter technology is particularly simple and advantageous. Such interdigital transducers which are applied to piezoelectric material can be used in the piezoelectric material by application of a frequency of e.g. some MHz up to some 100 MHz for the excitation of acoustic waves, in particular surface sound waves. They include comb-like metallic electrodes which engage into one another like fingers and which can be manufactured by photolithographic methods with a finger spacing in the range of e.g. 10 μm. Interdigital transducers are e.g. provided on piezoelectric crystals to excite surface sound waves thereon in a manner known per se, with twice the finger spacing of the metallic electrodes engaging into one another in the manner of a comb defining the wavelength of the surface sound waves which as a rule propagate perpendicular to the alignment of the finger electrodes. If such an interdigital transducer applied to a piezoelectric substrate is e.g. brought into contact with the vessel wall via a coupling medium, the period deformation of the surface stimulated in the piezoelectric material by application of a radio frequency to the interdigital transducer effects the generation of acoustic sound waves through the vessel wall and into the liquid.

The acoustic waves can e.g. be coupled in per se at the side wall of the vessel. Particularly symmetrical and simple relationships are obtained when the coupling takes place from below.

The speed at which a concentration in the vessel occurs depends inter alia on the geometry of the vessel, on the selected arrangement of the generation devices for the acoustic waves, on the radiated power of the acoustic waves, on the viscosity and on the filling level. The times, geometries and the external flow parameters such as the power, the frequency, the surface of the vessel wall through which the acoustic walls are radiated, the geometry of the vessel and the filling level can be optimized in an assay-specific manner.

The concentrated material can be withdrawn from the regions of minimal flow speed in which the material collects in the liquid. In this manner, the liquid with material of increased concentration can be moved e.g. into another vessel. Only one such volume element can in particular be transferred, e.g. with the help of a pipette, from the liquid in the vessel in which the flow speed is minimal and thus a locally increased concentration prevails after the concentration of the material. The transferred liquid then has an increased concentration. Typical volumes for such a concentration are e.g. between some µl and some 100 ml.

The concentration method in accordance with the invention can be used particularly advantageously to bring two types of reaction starting materials in a liquid so close to one another that the reaction probability is increased. The reaction starting materials collect in the regions in which the flow speed is minimal, is preferably equal to zero, and therefore come to a reaction faster than would be the case e.g. with a reaction method only determined by diffusion.

The reaction method can e.g. be used to examine cell-cell interactions in a solution or the reaction of cells with coated beads or the reaction of differently coated beads to one another. The reaction products which are in the regions of minimal flow speed can the be withdrawn directly, e.g. sucked out using a pipette. The reaction method in accordance with the invention, however, in particular provides the advantage that the reaction can be evaluated directly by direct observation of a region of minimal flow speed in which a reaction preferably takes place since the reaction partners are close to one another due to the concentration. This can take place e.g. with the help of optical methods, in particular by measurement of the fluorescent of the corresponding regions.

The reaction method in accordance with the invention can in particular be used such that both reaction starting materials of a reaction collect in the regions with minimal flow speed in order thus to increase the reaction probability. In another particularly advantageous embodiment, so-called beads are used, i.e. microspheres, of a diameter of some 100 nm up to some µm onto which one of the reaction starting materials is coated. This coated reaction material can e.g. be antibodies or antigens. If the corresponding complementary antigens or antibodies are in the liquid in which the beads are introduced, they bind to the coating of the beads and can lead to a linking of the beads. This agglutination can be evaluated optically so that a conclusion can be drawn on the presence of the antibodies or antigens with respect to the antigens or antibodies coated on the beads. By using the concentration method in accordance with the invention, the beads are concentrated in the regions of minimal flow speed such that the linking is promoted and accelerated.

The invention furthermore relates to a concentration device for the carrying out of the concentration method in accordance with the invention or the reaction method in accordance with the invention. The concentration device in accordance with the invention has a device or a plurality of devices for the generation of acoustic waves which is or are arranged such that a stationary flow pattern can be generated in the liquid by it or by them.

A concentration device in accordance with the invention can in particular be used in a correspondingly designed automatic apparatus in which the device or the devices for the generation of acoustic waves is/are controlled with the help of an automatic control. The control, for example, includes a microprocessor which is programmed such that the energy supply to the devices for the generation of acoustic waves is controlled such that the desired stationary flow pattern is adopted. The method procedure to be programmed which is required for this purpose can be determined, for example, in advance by experiments.

BRIEF DESCRIPTION OF THE DRAWING

The invention will be explained in detail with reference to FIG. 1 which shows an arrangement for the carrying out of the method in accordance with the invention in a schematic representation.

DESCRIPTION OF THE PREFERRED EMBODIMENTS

A liquid 10 in which e.g. beads coated with antibodies or antigens are located is located in the reaction vessel 12. In the embodiment shown, a piezoelectric substrate 16 is arranged at the bottom of the vessel as a noise generator which e.g. includes a lithium niobate crystal with an interdigital transducer 14 applied thereto. A coupling medium, e.g. water, oil, glycerin, silicone, epoxy resin or a gel film, to compensate irregularities and to ensure an ideal coupling is designated by reference numeral 18.

Electrical infeeds to a radio frequency source are provided for the connection of the electrodes of the interdigital transducer 14 in a manner known per se and are not shown in FIG. 1. The representation of the interdigital transducer 14 is only schematic. The number of the fingers of the interdigital transducer engaging into one another in a manner known per se is thus a great deal higher than shown. In FIG. 1, the lateral section through the finger electrodes of the interdigital transducer 14 engaging into one another like a comb is schematically indicated.

When an alternating electric field is applied to the electrodes of the interdigital transducer 14, a surface sound wave is generated in the piezoelectric crystal 16. This effects the generation of acoustic waves in the liquid 10 via the coupling medium 18 and the vessel wall.

The arrangement shown should include an interdigital transducer geometry which results in a directed radiation of acoustic waves into the liquid 10 in the direction of the arrow 15. This can e.g. be achieved by the selection of a unidirectionally radiating transducer radiating only in one direction.

Alternatively, e.g. a bidirectionally radiating interdigital transducer can be used which is not arranged symmetrically to the vessel. The arrangement is e.g. possible of a bidirectionally radiating interdigital transducer at a corner of the vessel so that only one of the two radiating directions is directed into the vessel. Finally, geometries can be realized with which a radiation direction of a bidirectionally radiating interdigital transducer can be absorbed or reflected directly.

In FIG. 1, 20 designates, in a schematic manner, a stationary flow which is generated by the radiation of acoustic waves in the direction of the arrow 15. 22 and 24 designated already concentrated material in the liquid 10, e.g. coated beads.

The device shown can be used as follows. An example will be described at which specific antibodies should be detected in a liquid. For this purpose, beads are coated with the corresponding antigens to these antibodies and are introduced into the liquid 10 in the vessel 12. The application of an alternating electrical field at the unidirectionally radiating interdigital transducers 14 effects the radiation of a sound wave in the direction of the arrow 15. This results in the formation of a stationary flow pattern which is designated schematically by 20. The flow speed drops outwardly and inwardly from the flow path 20. The beads coated with the antigens collect in the regions of flow speed zero. This is shown schematically by the crosses with the reference numeral 22 for regions at the vessel wall and by the crosses with the reference numeral 24 for the center of the vessel. If antibodies corresponding to the antigens coated on the beads are present in the liquid 10, they bind to the antigens which are coated on the beads so that the beads can link to one another. This binding process is promoted and accelerated by the high concentration of the beads 22, 24 in the regions of minimal flow speed.

The linking or agglutination in the regions of minimal flow speed can be evaluated optically and can thus serve for the detection of the presence of the antibodies corresponding to the antigens coated on the beads.

In an embodiment which is not shown, no interdigital transducer is used, but rather a piezoelectric volume oscillator which is arranged e.g. such that an oblique coupling of the sound wave takes place.

REFERENCE NUMERAL LIST 10 liquid with concentrated material
12 vessel
14 interdigital transducer
15 direction of radiated acoustic waves
16 piezoelectric substrate
18 coupling medium
20 stationary flow path
22, 24 concentrated material

The invention claimed is:

1. A concentration method for the concentration of material in a liquid, the method comprising:
   introducing a liquid into a vessel, the liquid comprising a material;
   radiating acoustic waves into the liquid such that a circular stationary flow pattern having regions of different flow speed arises in the vessel; and
   removing the material that collects in regions of said flow pattern having a flow speed close to or equal to zero.

2. A concentration method in accordance with claim 1, wherein acoustic waves are radiated into the liquid at one location and/or in one direction.

3. A concentration method in accordance with claim 1, wherein the locations of the radiation and/or the direction of the radiation of the acoustic waves are selected such that a plurality of regions are created in the liquid with the flow speed close to zero.

4. A concentration method in accordance with claim 1, wherein at least one interdigital transducer is used on a piezoelectric substrate for radiating the acoustic waves.

5. A concentration method in accordance with claim 1, wherein at least some of the acoustic waves are radiated into the liquid from below.

6. A concentration method in accordance with claim 1, wherein the step of removing the material is carried out with a pipette.

7. A concentration method in accordance with claim 1, wherein the flow speed is zero.

8. A concentration method in accordance with claim 1, wherein the flow speed is zero.

9. A reaction method for the reaction of at least two reaction starting materials in a liquid, the method comprising:
   concentrating the liquid using a concentrating step in which a liquid with the at least two reaction starting materials located therein is introduced into a vessel;
   wherein the concentrating step is carried out by radiating acoustic waves into the liquid such that a circular stationary flow pattern having regions of different flow speed arises in the vessel, and
   collecting the at least two reaction starting materials in regions of said flow pattern having a flow speed close to or equal to zero, thereby allowing the reaction of the at least two reaction materials.

10. A reaction method in accordance with claim 9, wherein at least one of the reaction starting materials is coated on beads.

11. A reaction method in accordance with claim 10, wherein the reaction is evaluated by observation of the agglutination or aggregation of beads which is made possible by the reaction of the at least one reaction starting material coated onto the beads with a reaction starting material in the liquid.

12. A reaction method in accordance with claim 9, wherein the reaction is evaluated by observation of at least one region of a flow speed close to or equal to zero.

13. A reaction method in accordance with claim 12, wherein the reaction is evaluated with the help of optical methods.

14. A reaction method in accordance with claim 13, wherein the optical methods comprise measurement of fluorescence.

15. A reaction method in accordance with claim 9, wherein the flow speed is zero.

* * * * *